(12) United States Patent
Wieland et al.

(10) Patent No.: US 7,306,950 B2
(45) Date of Patent: Dec. 11, 2007

(54) COMPOSITION AND USE OF SUBSTANCES FOR STABILISING AMINO ACIDS CONTAINING SULPHUR

(75) Inventors: Heinrich Wieland, St. Peter (DE); Emanuel Bissé, Denzlingen (DE)

(73) Assignee: Heinrich Wieland, St. Peter (DE)

( * ) Notice: Subject to any disclaimer, the term of this patent is extended or adjusted under 35 U.S.C. 154(b) by 608 days.

(21) Appl. No.: 10/478,570

(22) PCT Filed: May 15, 2002

(86) PCT No.: PCT/EP02/05368

§ 371 (c)(1),
(2), (4) Date: Nov. 20, 2003

(87) PCT Pub. No.: WO02/094248

PCT Pub. Date: Nov. 28, 2002

(65) Prior Publication Data

US 2004/0138169 A1    Jul. 15, 2004

(30) Foreign Application Priority Data

May 21, 2001    (DE) ................................ 101 24 820

(51) Int. Cl.
*G01N 33/48*    (2006.01)
*G01N 33/68*    (2006.01)
*A61K 31/7076*    (2006.01)

(52) U.S. Cl. .............................. 436/89; 436/8; 436/18; 436/63; 436/86; 436/176; 514/46; 252/408.1; 435/2; 435/15; 435/18

(58) Field of Classification Search .................... 436/8, 436/18, 63, 86, 89, 176; 514/46; 252/408.1; 422/73, 102; 435/2, 15, 18
See application file for complete search history.

(56) References Cited

U.S. PATENT DOCUMENTS 4,148,888 A * 4/1979 Cantoni et al. ............... 514/45
4,386,093 A * 5/1983 Chiang et al. ............... 514/303
4,968,690 A 11/1990 Marquez et al.
5,872,104 A 2/1999 Vermeulen et al.
6,309,885 B1 10/2001 Probst et al.

FOREIGN PATENT DOCUMENTS

| DE | 197 13 088 C 1 | 11/1998 |
| EP | 0 750 489 B1 | 11/1998 |
| EP | 1 085 083 A1 | 3/2001 |
| JP | 56051414 | 5/1981 |
| WO | WO 00/13691 | 3/2000 |
| WO | WO 00/78311 A1 | 12/2000 |
| WO | WO 01/81920 A2 | 11/2001 |

OTHER PUBLICATIONS

"Stabilisation of homocysteine in whole blood", Al-Khafaji, et al., Proceedings ACB National Meeting 1998, p. 21, Glasgow, May 11-15, 1998.
"Evaluation of NaF as a preservative in homocysteine measurements", Carlson, et al., Clinical Chemistry, vol. 44.
"S-Adenosyl-L-homocysteine Hydrolase Inhibitor Mediates Immunosuppressive Effects in Vivo: Suppression of Delayed Type Hypersensitivity Ear Swelling and Peptidoglycan Polysaccharide-Induced Arthritis", Saso, et al., The Journal of Pharmacology and Experimental Therapeutics, JPET 296:106-112, 2001.
"Acidic Citrate Stabilizes Blood Samples for Assay of Total Homocysteine", Willems, et al., XP-002225387, Clinical Chemistry 44, No. 2, 1998, pp. 342-345.
"Stabilization of blood homocysteine by 3-deazaadenosine", Al-Khafaji, et al., Am Cln Biochem 1998:35, pp. 780-782.
Rational approaches to the design of antiviral agents based on S-adenosyl-L-homocysteine hydrolase as a molecular target, Liu, et al., Antiviral Research, 19 (1992) 247-265.
"Pre-analytical Conditions Affecting the Determination of the Plasma Homocysteine Concentration", Clin Chem Lab Med 2001; 39(8): 675-680.

* cited by examiner

*Primary Examiner*—Maureen M. Wallenhorst
(74) *Attorney, Agent, or Firm*—George W. Neuner; Edwards Angell Palmer Dodge LLP

(57) ABSTRACT

The invention relates to a composition for the stabilization of sulphur-containing amino acids and/or for the inhibition of the continuous formation of sulphur-containing amino acids in withdrawn blood, to the use of suitable substances and compositions therefor as well as optionally for the determination of sulphur-containing amino acids in blood, to a process for these purposes, as well as to a blood collecting device applied appropriately to these processes.

82 Claims, 8 Drawing Sheets

COMPOSITION AND USE OF SUBSTANCES FOR STABILISING AMINO ACIDS CONTAINING SULPHUR

The invention relates to a composition for the stabilization of sulphur-containing amino acids in withdrawn blood, to the use of suitable substances and compositions therefor and optionally for the determination of sulphur-containing amino acids in blood, to a process for these purposes, as well as to a blood collecting device appropriately applied for this process.

In numerous prospective studies and case studies it could be shown in the last years that homocysteine in blood plasma represents an independent reversible risk factor for cardiovascular, atherosclerotic, neurologic and geriatric diseases. At about 8% of the general population and at 20-40% of patients with coronary or peripheral vascular diseases, a moderate increased plasma concentration of the homocysteine is found. A remarkable increase of the homocysteine is found with patients having homocysteineurea, which is based on inborn metabolism defects. The correlation between the plasma concentration of homocysteine and cardiovascular diseases is not definitely elucidated. The essential target point appears to be the endothelial cell. Homocysteine inhibits growth, decreases the activity of glutathione peroxidase, leads to changes of the gene expression, to a decreased expression of thrombomoduline, and to a decreased binding of the tissue plasminogen activator as well as to a decreased secretion of the "von-Willebrand"-factor. In addition, homocysteine may induce a proliferation of vascular smooth muscle cells. As a further harmful mechanism, the formation of free radicals by means of homocysteine in the presence of iron or copper ions is mentioned, that may lead to an oxidative modification of low density lipoproteins.

It is not clear whether homocysteine itself is responsible for the increased cardiovascular risk, because the mentioned mechanisms are based predominantly on data which have been obtained by means of animal tests and cell cultures. In these tests, rather high concentrations of homocysteine had been used (1-10 mmol/l). In addition, reduced homocysteine, i.e. the form which has been used in most of the "in-vitro"-studies, is present in concentrations of below 1 µmol/l.

A further problem of clinical trials heretofore resides in that the measured level of plasma homocysteine can only be taken as reliable, if the blood cells are centrifuged as fast as possible after the withdrawal of blood (<30 minutes) so that the serum can be obtained as fast as possible. This process, however, is not particularly practicable both for the established doctors and for the clinicians.

Therefore, this fastest possible obtainment of blood serum is required, because homocysteine is further produced by the blood cells even after the blood withdrawal (up to 40% increase of the concentration in the plasma after 1 hour). This is presumably based on that there are continuously transfers of methyl groups by means of S-adenosylmethionine in the blood cells. The formation of S-adenosylmethionine proceeds as long as serum or plasma is capable of providing methionine to the erythrocytes. Once S-adenosylmethonine has provided the methyl group, S-adenosyl homocysteine is produced thereby, which is then further hydrolized to homocysteine. Therefore, both the level of methionine in the serum and the duration until the obtainment of the serum have a considerable influence on the level of homocysteine in that serum. This may represent an important reason for the not much definite results with respect to the significance of the level of homocysteine for coronary and peripheric vascular diseases in human beings.

In order to determine homocysteine properly and reproducibly, the preanalytical requirements for a true determination of homocysteine must be satisfied, i.e. the continued formation of homocysteine should be discontinued.

Earlier studies in this field have been presented by F. Al-Khafaji, A. Bowron, A. Day, J. Scott and D. Stansbie in a lecture at the Congress of Association of Clinical Biochemists (ACB) (Proceedings ACB National Meeting 1998, Glasgow, $11^{th}$ to $15^{th}$ May 1998, p. 21). They reported that the inhibition of degradation of methionine to 2-adenosyl methionine was successful by means of NaF, and therefore no increase of homocysteine in the blood samples have been observed. With the inhibitor NaF, there was a decrease of the homocysteine level in blood in comparison with the initial value (at the time of withdrawing the blood), which is not desirable for a reliable preparatory analytical medicine.

Furthermore, the authors studied the effectiveness of 3-deazaadenosine, which is a known inhibitor for the S-adenosylhomocysteine hydrolase, on the stabilization of the homocysteine level. They reported that the reaction from S-adenosylhomocysteine to homocysteine can be effectively inhibited by this conventional inhibitor up to 72 hours.

This group of scientists published more detailed test results in a brief report (F. Al-Khafaji, A. Bowron, A. Day, J. Scott and D. Stansbie, *Ann. Clin. Biochem.*, 1998, 35, 780-782). It appeared that no increase of the homocysteine level in blood could be observed up to 24 hours by the addition of this conventional reversible and competitive inhibitor for the enzyme S-adenosylhomocysteine hydrolase. The increase of the homocysteine level of about 10% at a time of 72 hours after the blood withdrawal, which occurred in the further course, was also far below the comparison values of sampled vials which only contained the conventionally used anti-coagulant ethylenediamine tetraacetic acid (EDTA).

A problem which occurs when using 3-deazaadenosine resides in that noticable variations of the measured values occur, lying in the range of up to 2 µmol/l in 60 hours with homocysteine and in the range of up to 60 µmol/l in 60 hours with cysteine. Additionally, the amount of cysteinyl glycine and glutathione cannot be determined, because 3-deazaadenosine does not inhibit their formation. A further problem resides in that 3-deazaadenosine is not stable at room temperature and can be stored only in cooled state (+4° C.), which limits also its shipment capabilities. However, a simple handling of the reagents is of great importance in the diagnostic medicine, because for example withdrawn blood must be present in an unmodified form and transportable over an extended period without larger expenditure like, for example, cooling.

The object of the present invention is to improve the preparatory analytical medicine for the evaluation of sulphur-containing amino acids. In particular, the problems addressed in the prior art with respect to the variation of the levels of homocysteine and cysteine, the measurement of the amount of cysteinyl glycine and glutathione, an easy handling, storage and shipment capability should be solved.

This object is solved in a first aspect of the invention by the provision of a composition for the stabilization of sulphur-containing amino acids and/or for the inhibition of the continuous formation of sulphur-containing amino acids in blood, wherein the composition contains at least one, not only competitive inhibitor for at least one enzyme involved in the metabolic formation of homocysteine.

Alternatively, the object is solved according to a further aspect of the invention by the provision of a composition for the stabilization of sulphur-containing amino acids and/or for the inhibition of the continuous formation of sulphur-containing amino acids in blood, wherein an acid and at least inhibitor for an enzyme, which is involved in the metabolic formation of homocysteine, are contained in combination in the composition.

Further subject matters according to the invention are the use of an inhibitor of at least one enzyme, which is involved in the metabolic formation of homocysteine, for the stabilization of sulphur-containing amino acids and/or for the inhibition of the continuous formation of sulphur-containing amino acids in blood, wherein a not only competitive inhibitor for at least one enzyme which is involved and the metabolic formation of homocysteine is used as inhibitor. Furthermore, the use of the composition mentioned above in connection with the first and the second aspect for the stabilization of sulphur-containing amino acids and/or for the inhibition of the continuous formation of sulphur-containing amino acids in blood is a subject matter of the invention.

A further subject matter of the invention relates to a process for the stabilization of sulphur-containing amino acids and/or for the inhibition of a continuous formation of sulphur-containing amino acids in blood, and optionally to the determination of the amount of sulphur-containing amino acids and/or other blood components in the blood, wherein the blood is mixed after its withdrawal with a composition mentioned above in connection with the first or the second aspect, or with a not only competitive inhibitor for at least one enzyme, which is involved in the metabolic formation of homocysteine. The process can be embodied such that (a) the composition or the inhibitor is provided in a blood collecting device, (b) the withdrawn blood is delivered to the blood collecting device, optionally (c) the blood placed into the blood collecting device is stored for a desired period in which the sulphur-containing amino acids are present in a stabilized manner and/or the continuous formation for the sulphur-containing amino acids is inhibited, and optionally (d) the amount of the desired sulphur-containing amino acids and optionally further blood components in the blood sample is determined.

A further subject matter according to the invention is a blood collecting device comprising the substance according to the invention, or the composition according to the invention.

The above mentioned and further solutions of the object of the invention with their effects and advantages will become apparent from the following detailed description of the invention and from the preferred embodiments.

Next, the figures will be explained in more detail:

Figure 3:
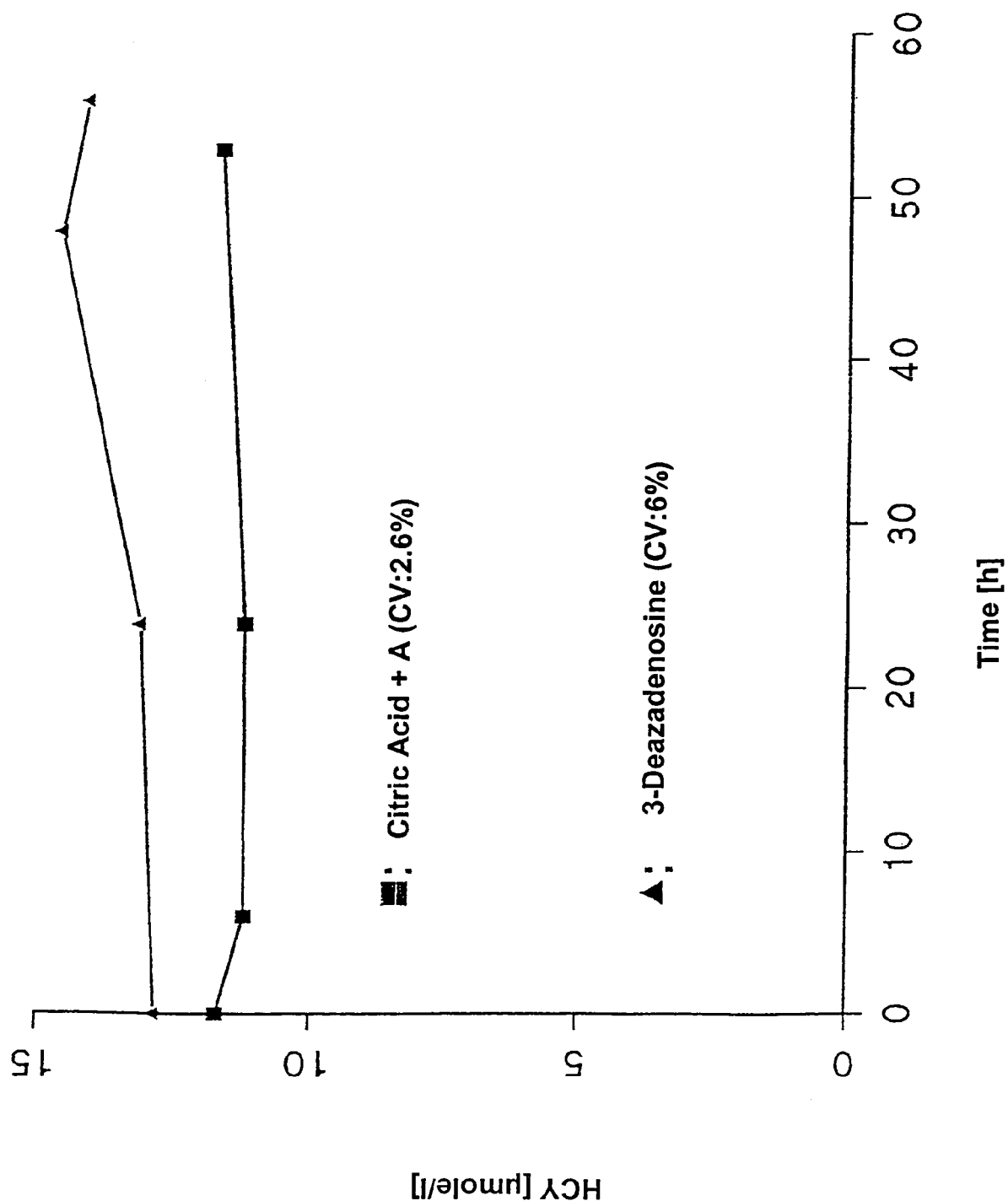

FIG. 3 illustrates the stabilization effects of citric acid+A (mixture of EDTA, 5(4)-aminoimidazole-4(5)-carboxamide and 2'-deoxyadenosine) and of 3-deazaadenosine with respect to the HCY-concentration. The samples were placed in EDTA vials containing citric acid+A or 3-deazaadenosine. They were kept at room temperature.

Figure 4:
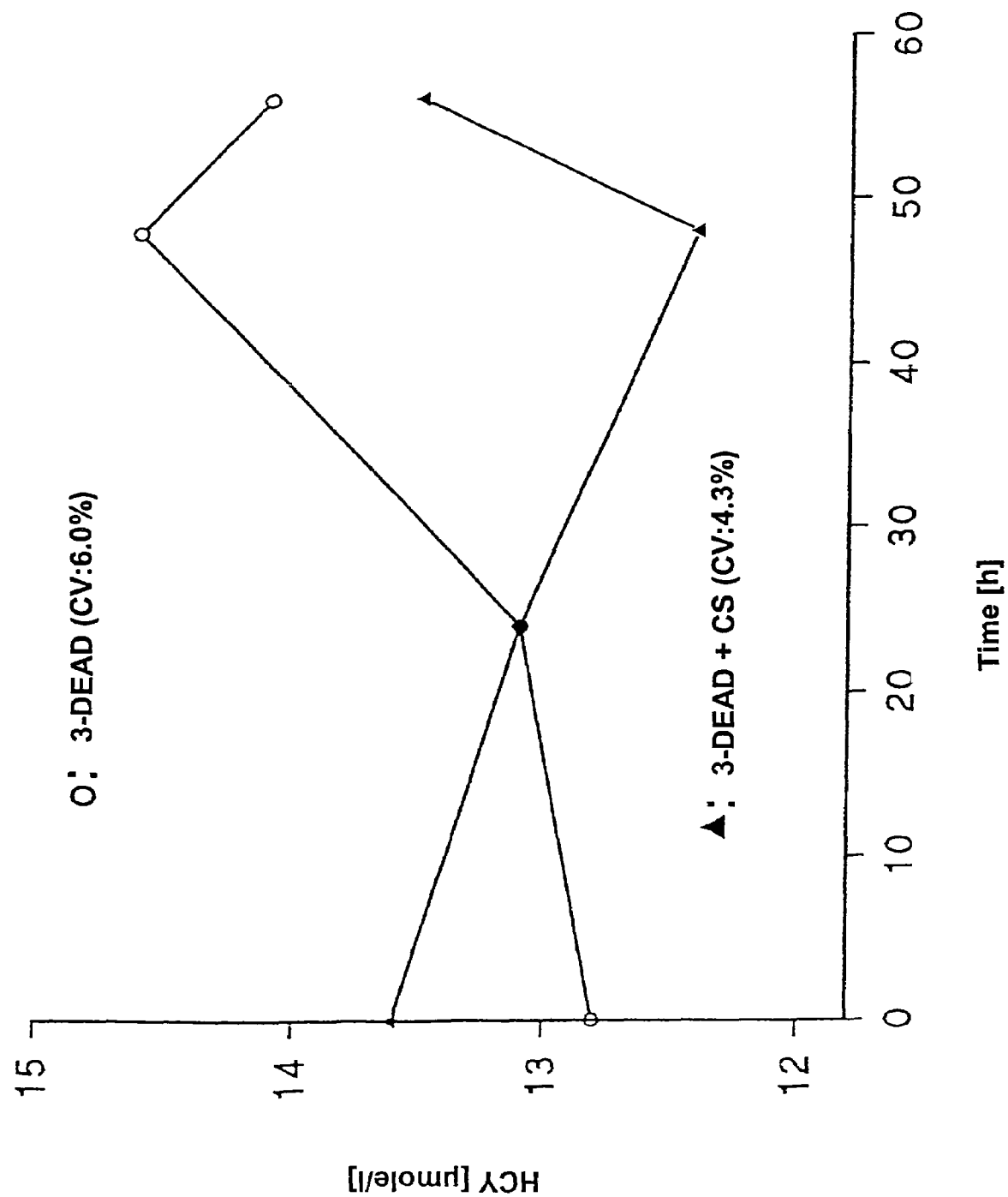

FIG. 4 illustrates the stabilization effects of citric acid+ 3-deazaadenosine (3-DEAD) and of 3-deazaadenosine on the HCY-concentration. The samples were placed in EDTA vials containing citric acid+3-DEAD or 3-DEAD. They were stored at room temperature.

Figure 5:
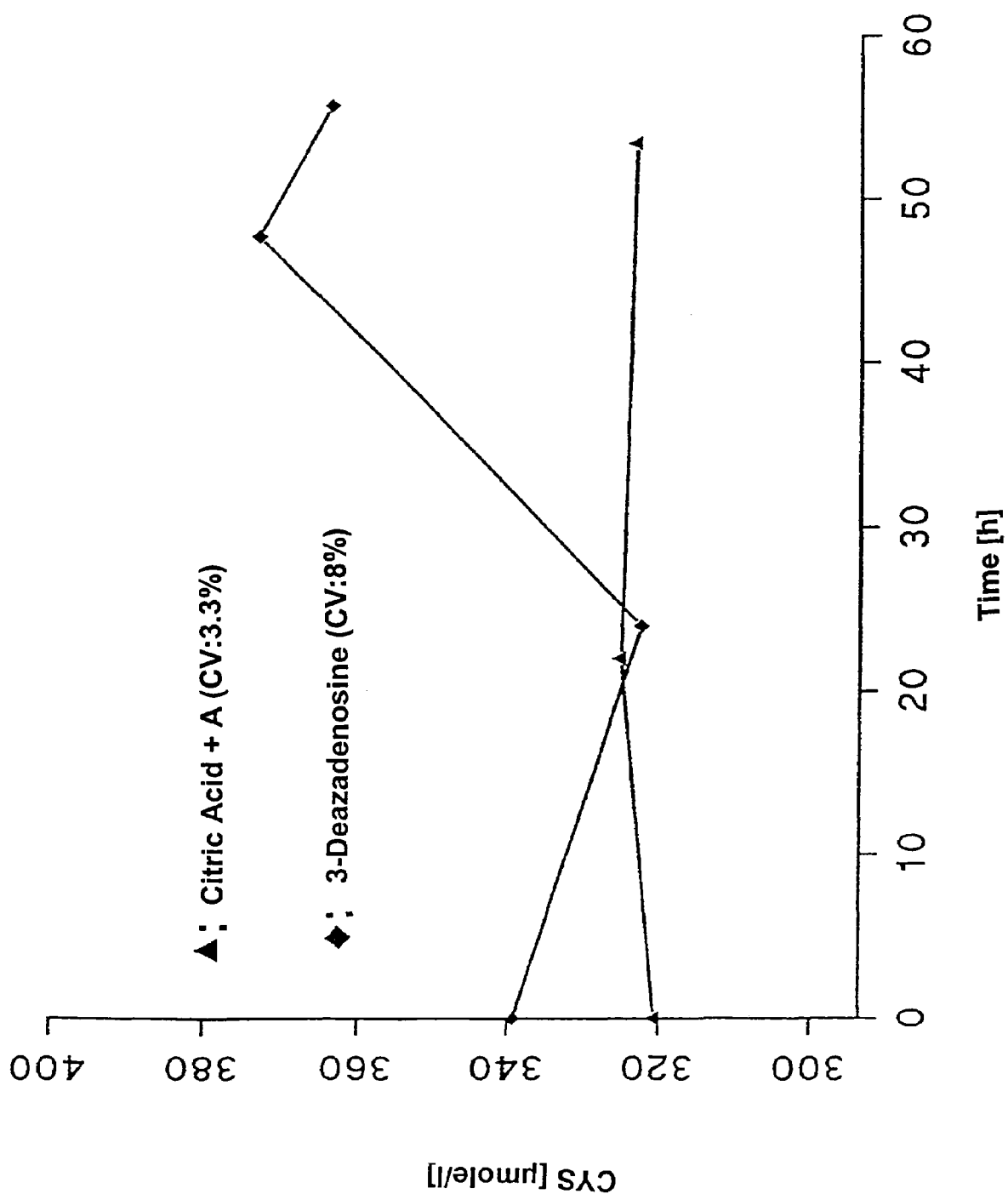

FIG. 5 illustrates the stabilization effects of citric acid+A and of 3-deazaadenosine on the concentration of cysteine (CYS). The samples were placed in EDTA vials containing citric acid+A or 3-deazaadenosine. They were stored at room temperature.

Figure 6:
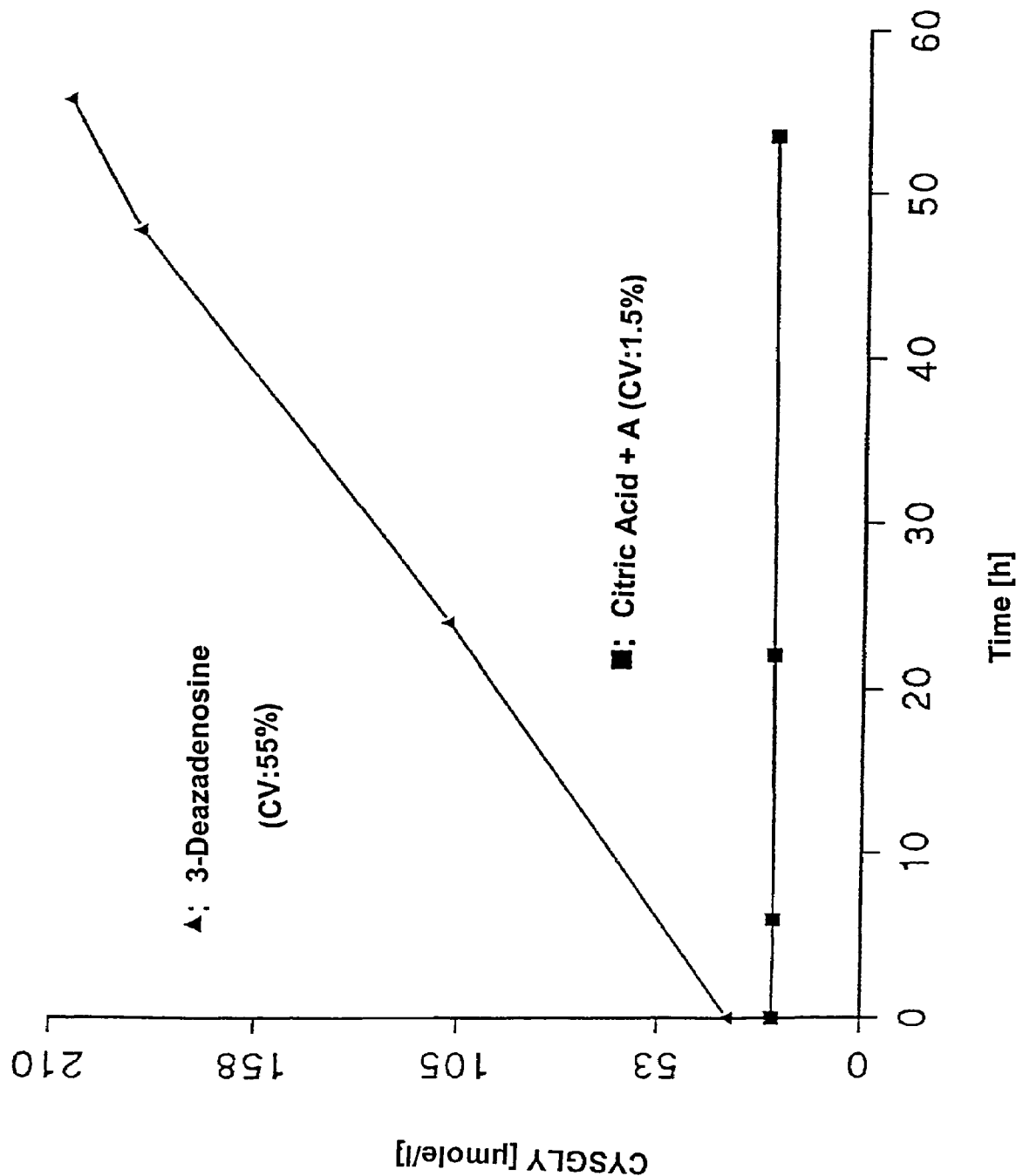

FIG. 6 illustrates the stabilization effects of citric acid+A and of 3-deazaadenosine on the concentration of cysteinyl glycine (CYSGLY). The samples were placed in EDTA vials containing citric acid+A or 3-deazaadenosine. They were stored at room temperature.

Figure 7:
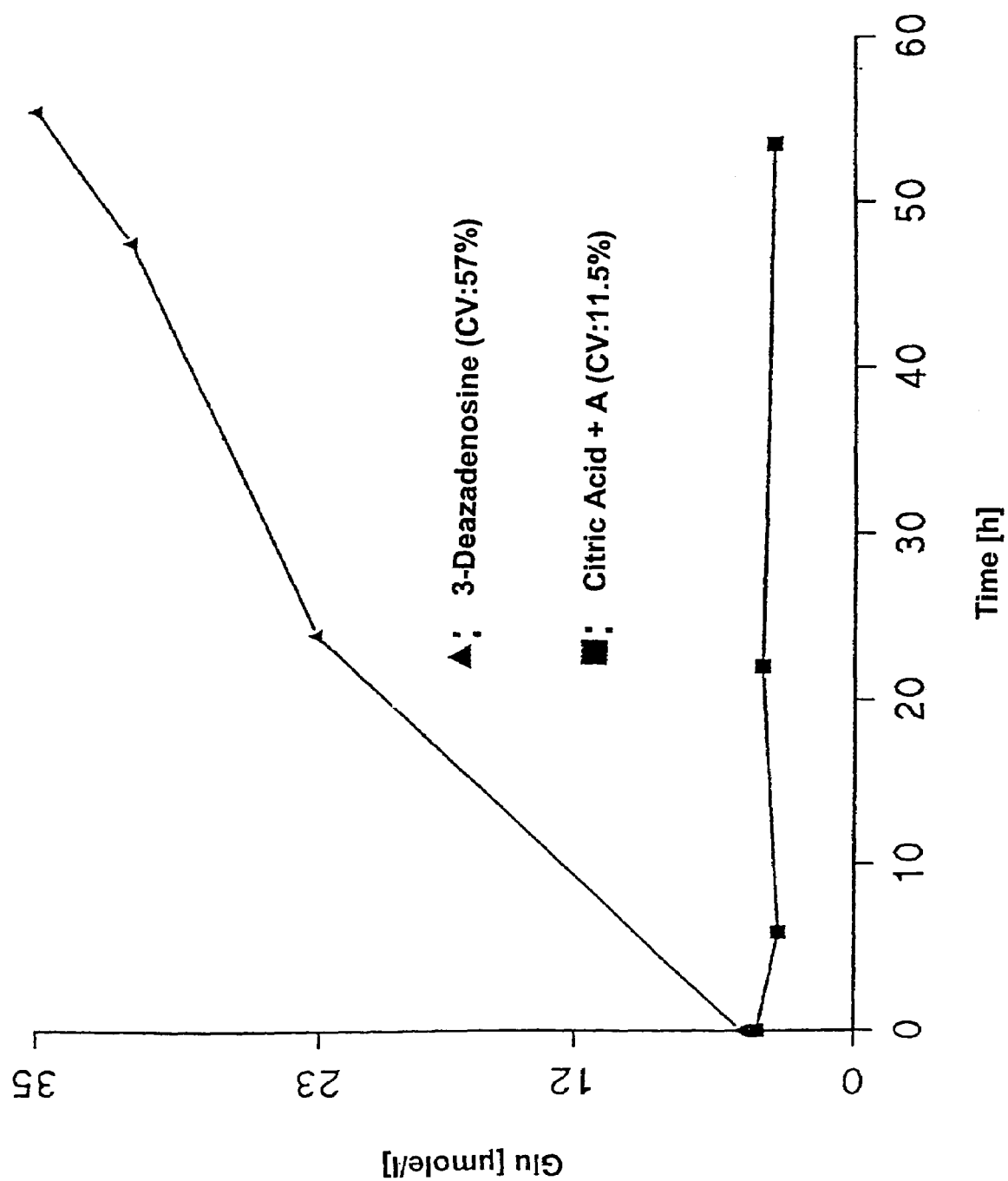

FIG. 7 illustrates the stabilization effects of citric acid+A and 3-deazaadenosine on the concentration of glutathione (GLU). The samples were placed in EDTA vials containing citric acid+A or 3-deazaadenosine. They were stored at room temperature.

Figure 8:
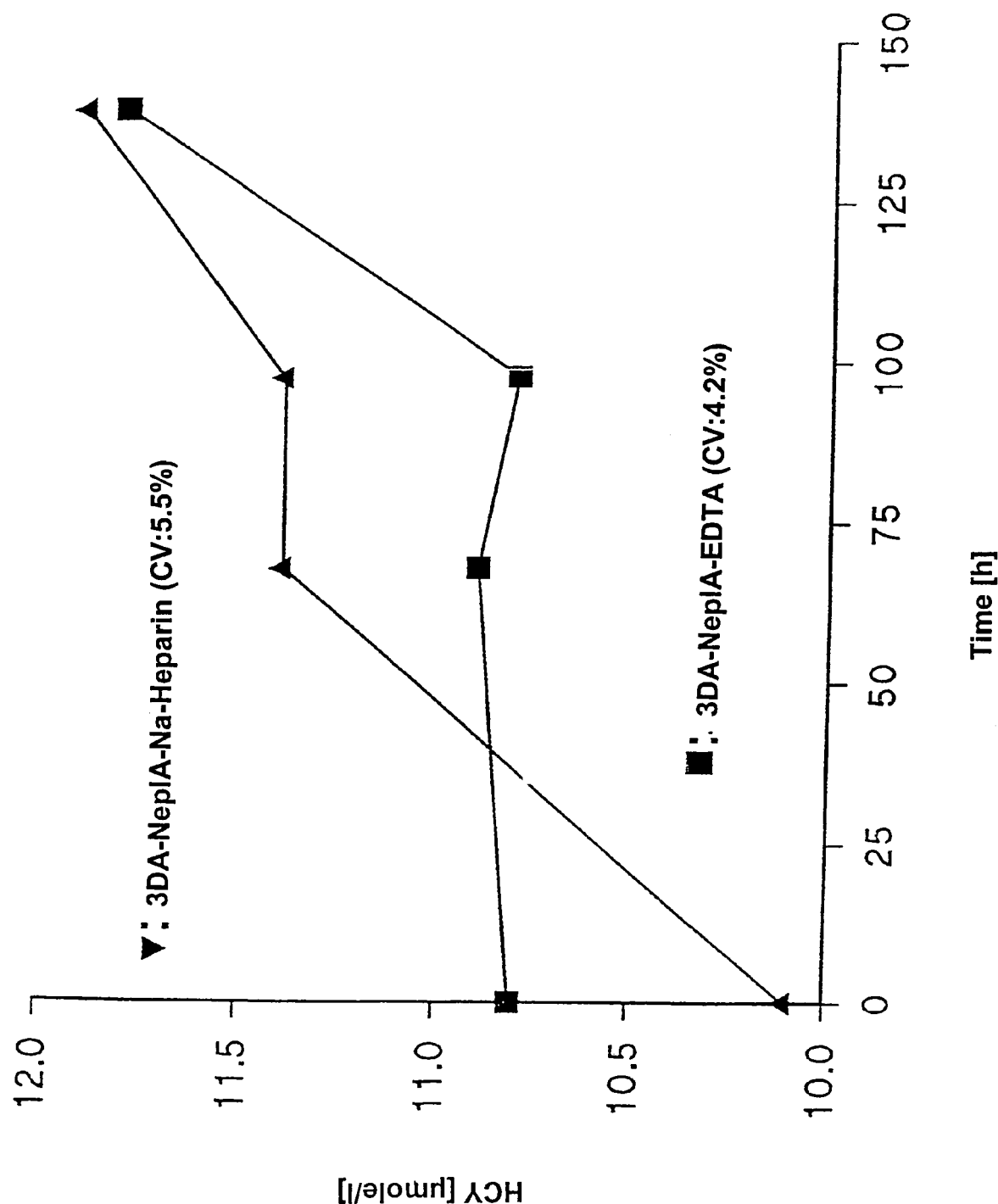

FIG. 8 illustrates the stabilization effects of 3-deazaadenosine A (3DA-NeplA) on the HCY-concentration. The samples were placed in EDTA vials and Na-heparin vials, each of which contained 3-DA-NeplA, and were stored at room temperature.

In the following, the effects and advantages of the invention as well as preferred embodiments of the present invention will be described, referring to the attached graphic illustrations.

The at least one inhibitor applied according to the present invention is one which inhibits an enzyme involved in the metabolic formation of homocysteine. Optionally the same inhibitor may be an inhibitor for a further enzyme involved in the formation of homocysteine. Preferably, an S-adenosylhomocysteine hydrolase, a methyl transferase, wherein S-adenosylmethionine serves as methyl donor, or any other enzyme involved in the formation of homocysteine or the degradation of homocysteine may represent targets for the inhibition.

The at least one inhibitor applicable for all aspects of the invention preferably has a structure of being non-ionic and/or such hydrophobic to be capable of permeating an erythrocyte membrane. The inhibitor thus is distinguished from the reagent NaF, or from indirect stabilizations carried out through calcium ion binding by means of chelate formers like EDTA or citrate. With this preferred inhibitor structure, a lysis of the blood cells is not necessary. Since in addition an avoidance of blood cell lysis is an advantage, no agents for lysis of blood cells are preferably used according to the present invention.

According to the first aspect of the invention, wherein the inhibitor achieves the desired effects also without acid, the applied inhibitor has not only a competitive inhibitory action towards an enzyme involved in the formation of homocysteine. Thus, this concept is significantly different from the conventionally used competitive inhibitory 3-deazaadenosine, which yet shows relative strong variations in the stabilization. The group of not only competitive inhibitory inhibitors preferably include irreversible inhibitors and in particular so-called suicide inhibitors. It is advantageous if, among the possible enzymes involved in the formation of homocysteine, the enzyme S-adenosylhomocysteine hydrolase is inhibited by a corresponding inhibitor. Those inhibitors which lead to an inactivation of S-adenosylhomocysteine hydrolase with a depletion of the co-factor $NAD^+$ are above all to be used as being particularly effective in terms of the first aspect of the invention. Examples for advantageous inhibitors include neplanoncin A, 3-deazaneplanocin A, 9-(trans-2'-, trans-3'-dihydroxycylopent-4'-enyl)-adenosin (DHCeA), 3-deaza-DHCeA, 9-(trans-2'-, trans-3'-dihydroxycylopentanyl)-adenosin (DHCaA), 3-deaza-DHCaA, β-4'-methyl-DHCaA, β-4'-vinyl-DHCaA (Z- or E)-4', 5'-didehydro-5'-deoxy-5'-fluoro-adenosin (Z-DDFA or E-DDFA) and 5'-deoxy-5'-difluoro-adenosin (DFA) as well as the inhibitory derivatives or analogs of the mentioned compounds. These inhibitors are comprehensivly described, as so-called S-adenosylhomocysteine hydrolase inhibitors of the second generation, by S. Liu, M. S. Wolfe and R. T. Borchardt in *Antiviral Research* 19 (1992), p. 247-265 as antiviral agents. It is assumed that the reason for the significant difference over the only competitive inhibition resides in that the mentioned inhibitors bring about a depletion of available co-factor $NAD^+$, with an oxidation of the applied inhibitor to the 3-keto form, and optionally a stable bond of the oxidized 3'-keto form in the enzyme.

Additional advantageous effects can be achieved by means of further additives. Thus, it was surprisingly found in the framework of the second aspect that a cheap solution of the problem of the invention can be achieved with almost the same effect by means of a composition according to the second aspect of the invention. By means of a composition which, besides at least an inhibitor for an enzyme involved in the formation of homocysteine, additionally comprises at least one acid, an improved stabilization of sulphur-containing amino acids and/or an improved inhibition of the formation of sulphur-containing amino acids in blood can be achieved. In this case even a conventional competitive inhibitor such as 3-deazaadenosin is usable due to the obtained synergistic effect with the help of the acid.

The inhibitors for the at least one enzyme involved in the formation of homocysteine used in these compositions according to the invention to be combined with an acid may be selected from the following group:

2'-deoxyadenosin (DEOA), 5(4)-aminoimidazol-4(5)-carboxamid (5(4)-AMCA), 9(S)-(2,3-dihydroxypropyl)-adenosin ((S)-DHPA), (R,S)-3-adenin-9-yl-2-hydroxypropanic acid ((R,S)-AHPA), adenine-dialdehyd, 3-deazaadenosin, 5-deoxy-5-methyl-thioadenosin, 5-deoxy-adenosin (aristeromycin), neplanocin A, 3-deazaneplanocin A, 9-(trans-2'-,trans-3'-dihydroxyclopent-4'-enyl)-adenosin (DHCeA), 3-deaza-DHCeA, 9-(trans-2'-, trans-3'-dihydroxycylopentanyl)-adenosin (DHCaA), 3-deaza-DHCaA, β-4'-methyl-DHCaA, β-4'-vinyl-DHCaA, Z- or E-4',5'-didehydro-5'-deoxy-5'-fluoro-adenosin (Z-DDFA or E-DDFA) and 5'-deoxy-5'-difluoro-adenosin (DFA) as well as the inhibitory derivatives or analogs of the mentioned compounds. Concerning the compounds, known per se as antiviral agents, it is again referred to the above mentioned review article of S. Liu, M. S. Wolfe and R. T. Borchardt in *Antiviral Research* 19 (1992), 247-265 (with further citations).

As for the inhibitors which are particularly suitable for the second aspect of the invention there are mentioned 3-deazadenosin, 5-deoxy-5-methyl-thioadenosin and the inhibitory derivatives thereof, as well as the preferably irreversible inhibitors of said enzymes such as neplanocin A and 3-deazaneplanocin A and the inhibitory derivatives of the compounds mentioned in connection with the first aspect of the invention.

The acids according to the second aspect of the invention, which are applied in the composition independent from the type of the inhibitor, there are preferably organic acids and above all those which do not cause lyses of erythrocytes. The acid is preferably selected, alone or in combination, from the following group: ascorbic acid, citric acid, citramalic acid, citraconic acid, fumaric acid, lactic acid, oxalic acid, tartaric acid and other organic mono-, di- and higher valanced acids. The occurrence of an erythrocyte lysis would falsify the preparatory analytical medicine on the basis of a dilution effect caused thereby. The most preferred acid is citric acid.

The acid may be added to the composition basically in any desired form. However, the inventors surprisingly found that the stabilization effect on the sulphur-containing amino acids is favored, if the acid is present in the composition in solid form and preferably powdered. The acid applied in the composition according to the invention had particularly favorable effects, if it was present in a lyophylized form.

By means of the compositions of the invention, not only the amount of homocysteine and cysteine in withdrawn blood with lower variations compared to conventional stabilization systems, but also the amount of cysteinyl glycine and glutathione can be stabilized in a constant manner up to 54 hours, preferably up to 72 hours and partially even up to 100 hours and above (e.g. a stabilization of homocysteine of at least 143 hours at room temperature with 3-deazaneplanocin A). In addition, the blood samples mixed with the composition of the invention are storable and can be shipped over a longer period at room temperature.

A combination of one or more competitive inhibitor(s) and/or one or more irreversible inhibitor(s) for the previously mentioned enzymes may be advantageous for the stabilization of the homocysteine level in whole blood because of the favorably added effect. This is particularly effective in the case when at least one inhibitor of the methyl transferase and/or at least one competitive or non-competitive inhibitor of the S-adenosylhomocysteine hydrolase is or are present. In particular, good results have been achieved by means of a combination of the two inhibitors 2'-deoxyadenosin and 5(4)-aminoimidazol-4(5)-carboxamid.

In addition, the composition of the invention also may contain any further additive which is conventionally used in compositions for the preparatory analytical medicine of blood.

For example, the adjustment of the pH-value to a physiologically favorable value is useful for the composition of the invention. Therefore, a buffer may be added to the composition of the invention, for example in solid, liquid or lyophylized form. The proportion of buffer is determined such that it exhibits a sufficient buffering effect after its mixture with the substance, in order to adjust the pH value to a range of about pH 5 to about pH 9, preferably about pH 6 to pH 8 and particularly about pH 6.5 to about pH 7.5. The use of a conventional phosphate buffer and preferably a phosphate buffer on the basis of di-sodium phosphate, for example in a range of 0.001 mole/l to 1 mole/and preferably from 0.005 mole/l to 0.05 mole/l and particularly in a range of round approximately 0.01 mole/l has been shown to be favorable for the stabilization of sulphur-containing amino acids. For example, compounds among the group consisting of NaCl, benzoic acid and further commonly used buffer components may be added to the buffer mixture.

Further additives may be added to the composition of the invention, particularly anti-coagulants such as EDTA, heparin (e.g. sodium heparinate), citrate (e.g. sodium citrate), which counteract blood blotting. Furthermore, other typical plasma stabilizers such as Euxyl have a favorable effect. Yet other conventionally used auxiliary agents and additives, such as reagents for the determination of further blood components, confer useful properties to the composition.

The composition of the invention is preferably present in solid form, in lyophylized form or as liquid, for example dissolved in water.

The composition of the invention as previously characterized is applied according to the invention for the stabilization of sulphur-containing amino acids and/or for the inhibition of the continuous formation of sulphur-containing amino acids in blood, e.g. in withdrawn whole blood, in blood plasma or in blood serum or also in other body fluids such as urine.

According to the invention, an inhibitor, as long as it relates to the first aspect of the invention, yet can be used alone for at least one of the enzymes involved in the metabolic formation of homocysteine for the stabilization of sulphur-containing amino acids and/or for the inhibition of the continuous formation of sulphur-containing amino acids in blood. In this respect, it is referred to the above description with respect to the inhibitors suitable for the first aspect of the invention as well as with respect to the combination of several such inhibitors.

The use of either the inhibitor alone or the composition of the invention aims at the stabilization of the sulphur-containing amino acids in blood. Thus, the blood, which is present in suitable blood samples, may be stored, after the admixture with the inhibitor or the composition of the invention, for a sufficient period and thus may be tested not before several hours or days after the withdrawal of the blood. Essential advantages of the preparatory analytical medicine result from longer storage resistance, extended possibilities of the preparatory analytical medicine, particularly the temporal separation of blood withdrawal and blood measurement for the sulphur-containing amino acids as well as the transport of the blood samples, and the ensurance of constant values for the measured amino acids also after the storage at room temperature over an extended period.

The use of the inhibitors or the compositions of the invention will be particularly applied for the preparatory analytical medicine and the determination of sulphur-containing amino acids such as homocysteine, cysteine, ciysteinyl glycine, glutathione and their derivatives in blood.

When using the acid-containing composition of the invention, the concentration of the acid is preferably adjusted to a range of from 2 to 10 mg per 1 ml of whole blood to be tested.

The amount of the single or combined inhibitors, or the inhibitors contained in the composition is suitably adjusted such that an amount of 15 to 210 µg and preferably form 20 to 100 µg is used per 1 ml of the whole blood to be tested.

In the process according to the invention for the stabilization of sulphur-containing amino acids in blood, in step (a) either the inhibitor used alone or in combination, or the composition of the invention according to the described first or second aspect is provided in a pre-determined amount in the blood collecting device. The amount of inhibitor or of the composition is determined in a manner that the previously mentioned concentration ranges for the inhibitor and optionally the acid are adjusted with respect to the blood sample withdrawn or to be measured.

Subsequently, in step (b) the withdrawn blood is delivered to the blood collecting device, and the obtained mixture is directly mixed. The faster this mixture is carried out after the blood withdrawal, the better is the preparatory analytical medicine and therefore the subsequent analysis or analytical medicine of the sulphur-containing amino acids.

In step (c) the blood being placed into a blood collecting device and being mixed with the inhibitor or the composition of the invention may be stored for a desired period, during which the sulphur-containing amino acids are present in a stabilized form, or the continuous formation of the sulphur-containing amino acids is inhibited. The achievable storage periods depend on the inhibitor or composition used and usually lie in the range of 48 to 72 hours, but can also lie in a range of above 100 hours.

After the storage, analysis or analytical medicine of the sulphur-containing amino acids and optionally, as desired, of further blood components may optionally be carried out. The determination of the desired amino acids is usually carried out in the blood itself, e.g. from the whole blood the blood plasma and/or the blood serum. For the analysis or analytical medicine any one of the processes known in the prior art may be used, such as for example the determination by means of HPLC or by means of an enzyme immunoassay. Determination processes being respectively based on immunological testing are preferred.

The process according to the invention may also be carried out in a manner that not the inhibitor or the composition containing the inhibitor is provided in the blood collecting device, but the used substance is added as fast as possible only after providing the blood sample. Accordingly, any conceivable kind of blood withdrawal is possible, if the blood is contacted and mixed immediately after its withdrawal with the inhibitor or the composition according to the invention.

Depending on which order the process of the invention is carried out, it may be necessary to use different blood collecting devices.

According to the invention a blood collecting device comprises either the inhibitor used alone or a combination of inhibitors, or a composition according to the invention. By means of providing the inhibitor or the composition in the blood collecting device in a solid, a powder-like, a liquid or a lyophylized form, the withdrawn blood may be mixed with the provided substance as fast as possible. The blood collecting device may comprise the single inhibitor or the composition also in supported form.

The blood collecting device is preferably designed with a device which can be connected either directly or through a tubing, with a conventional blood withdrawal device such as an injection needle or a Braunule, in order to bring the withdrawn blood immediately in contact with the inhibitory substance. Therefore, it is preferred that the blood collecting device is designed in the form of a monovette, which comprises the single inhibitor or the composition of the invention in a desired form.

The monovette, which is filled with blood and the inhibitor or the composition, may be closed and, without cooling, stored and shipped.

Next, the invention will be explained in more detail by the following examples, however, without limiting the invention thereto.

EXAMPLES 1 TO 15 AND COMPARATIVE EXAMPLES 1 TO 3

Material Used and Processes

The following inhibitors of methyl transferase or S-adenosylhomocysteine hydrolase have been tested
1 5(4)-aminoimidazol-4(5)-carboxamide (5(4)-AMCA)
2 2'-deoxyadenosin (DEOA)
3 5-deoxy-5-methyl-thioadenosin (5-DEMET)
4 3-deazaadenosin (3-DEAD)
5 neplanocin A (NeplA)
6 3-deazaneplanocin A (3DA-NeplA).

The effectiveness of the inhibitors have been tested in combination with the following acids:
1 ascorbic acid (VitC)
2 citric acid (CS)
3 citramalic acid (CMS)
4 citraconic acid (COS)
5 ethylenediamine tetraacetic acid (EDTA)
6 fumaric acid (FS)
7 lactic acid (MS)
8 oxalic acid (OS)
9 tartaric acid (WS).

The compositions of further reagents have been:
Mixture A: 5(4)-AMCA (5.2 mg) and DEOA (3.2 mg), dissolved in 500 µl phosphate buffer.
Composition of the buffer for mixture A:
0.01M $Na_2PO_4$, 0.15M NaCl, 0.1% benzoic acid, 0.1% Euxyl k100.
All other substances have been dissolved in water.

Blood Withdrawal and Treatment of Samples

Corresponding amounts of stabilizers have been provided in EDTA- or Na-heparin-monovettes for each Example or Comparative Example (see Table 1). The blood withdrawal has been carried out in monovettes with and without stabilizers. For the control value, the monovettes have been centrifuged within 30 minutes after withdrawal.

Results

The results for the examples and comparative examples are to be gathered from Table 1 and FIGS. 1 to 8.

samples by 3-deazaadenosin. When using exclusively 5(4)-aminoimidazol-4(5)-carboxamid or 2'-deoxyadenosin, no significant stabilization of sulphur-containing amino acids has been achieved. This suggests that the inhibitory effect of these substances is enhanced in the presence of proton donors.

In these tests, 3DA-NeplA shows the best results (143 hours, variation coefficient VK<5%) with respect to the stabilization of HCY in whole blood.

TABLE 1

|  |  | Amount # | CYS-SD | HCY-SD | CYSGLY-SD | GLU-SD |
|---|---|---|---|---|---|---|
| Ex. 1 | CS + A | 6.3 mg + 25 µl | 72 h (VK: 17%) | 103 h (VK: 6.6%) | (−) | (−) |
| Ex. 2 | CS* + Aˢ | 6.3 mg + 25 µl | 48 h (VK: 3.5%) | 48 h (VK: 2.1%) | (−) | (−) |
| Ex. 3 | CS§ + A | 6.3 mg + 25 µl | 54 h (VK: 3.3%) | 54 h (VK: 2.6%) | 54 h (VK: 1.6%) | 54 h VK: 11%) |
| Ex. 4 | CS§ + Aˢ | 6.3 mg + 25 µl | 73 h (Vk: 17%) | 73 h (VK: 7.2%) | 24 h (VK: 35%) | (−) |
| Cmp.-Ex. 1 | 3-DEAD | 0.107 mg | 56 h (VK: 7.6) | 56 h (VK: 6%) | (−) | (−) |
| Ex. 5 | 3-DEAD + CS§ | 0.07 mg + 6.3 mg | 48 h (VK: 3.6%) | 56 h (VK: 4.3%) | (−) | (−) |
| Ex. 6 | 3-DEAD + CS§ + A | 0.107 mg + 6.3 mg + 25 µl | 24 h (VK. 3.5%) | 24 h (Vk: 2.1%) | (−) | (−) |
| Cmp.-Ex. 2 | VitC | 6.3 mg | 73 h (VK: 11%) | 73 h (VK: 8%) | 73 h (VK: 5%) | (−) |
| Ex. 7 | VitC + A | 6.3 mg + 25 µl | 72 h (VK: 10%) | 73 h (VK: 12%) | 73 h (VK: 12%) | 73 h VK: 15%) |
| Ex. 8 | MS + A | 2.8 mg + 25 µl | 72 h (VK: 7.5%) | 48 h (VK: 7.3) | (−) | 72 h (VK: 6.7%) |
| Ex. 9 | CMS + A | 3.8 mg + 25 µl | 49 h (VK: 3.8%) | 72 h (VK: 7%) | 72 h (VK: 7.5%) | (−) |
| Ex. 10 | COS + A | 3.8 mg + 25 µl | 72 h (VK: 0.5%) | 72 h (VK: 3.0%) | (−) | (−) |
| Ex. 11 | 5-DEMET + A | 5 mg + 25 µl | 49 h (VK: 9%) | 49 h (VK: 15%) | (−) | (−) |
| Cmp.-Ex. 3 | FS | 3.8 mg | 47 h (VK: 4%) | 47 h (VK: 8%) | (−) | (−) |
| Ex. 12 | FS + A | 6.3 mg + 25 µl | 44 h (VK: 4.5%) | 44 h (VK: 5%) | (−) | (−) |
| Ex. 13 | NeplA | 60 µg | (!) | 70 h VK(4.5%) | (!) | (!) |
| Ex. 14 | 3DA-NeplA | 30 µg | (!) | 143 h (VK4.2%) | (!) | (!) |
| Ex. 15 | OS + A | 3.5 mg | 72 h (VK: 3.5%) | 72 h (VK: 4.5%) | (−) | (−) |

Figure 1:
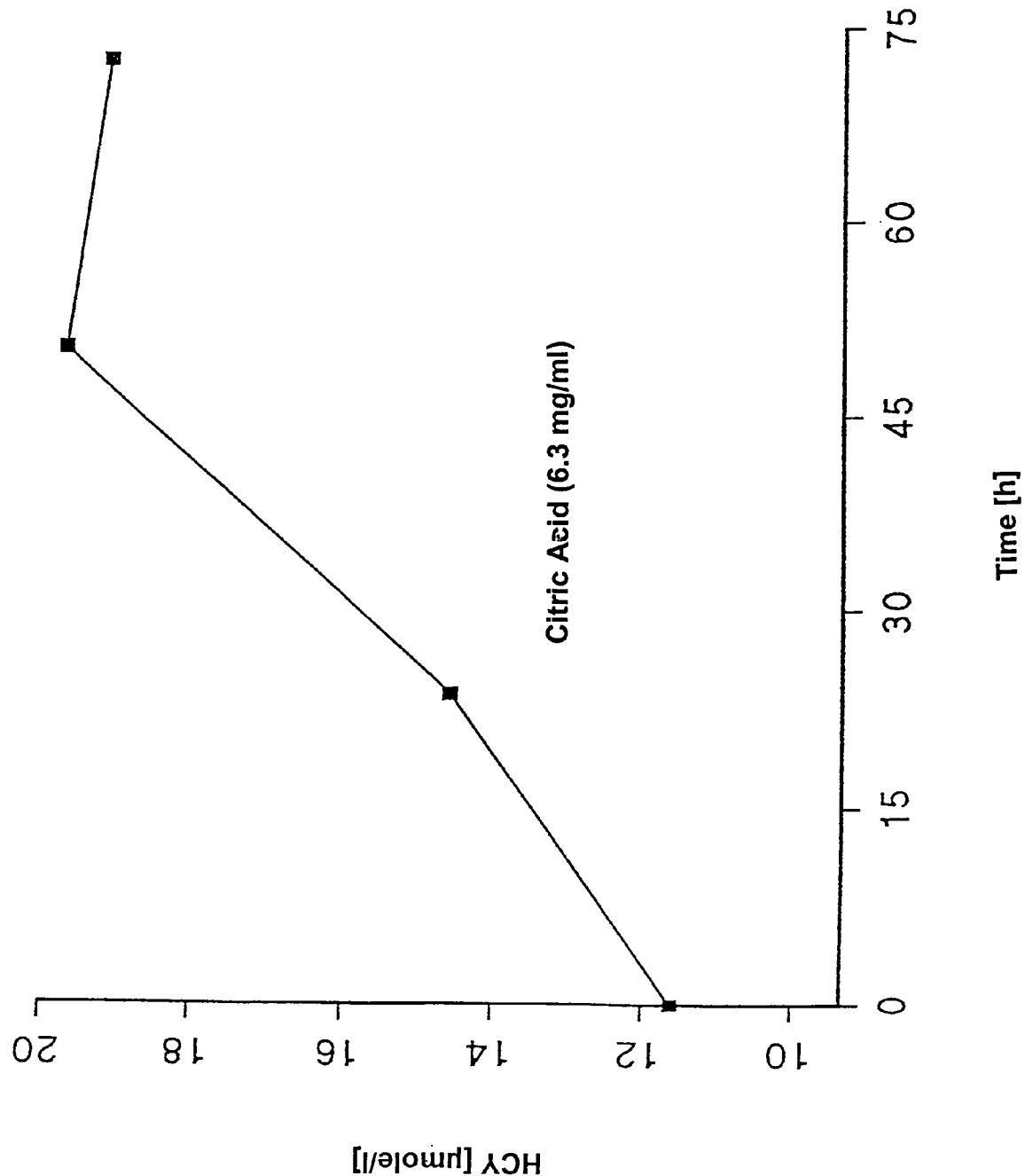
FIG. 1 illustrates the increase of the concentration of homocysteine (HCY) in whole blood, which has been collected in vials containing ethylenediamine tetraacetic acid (EDTA) and citric acid. The samples where kept at room temperature.
Figure 2:
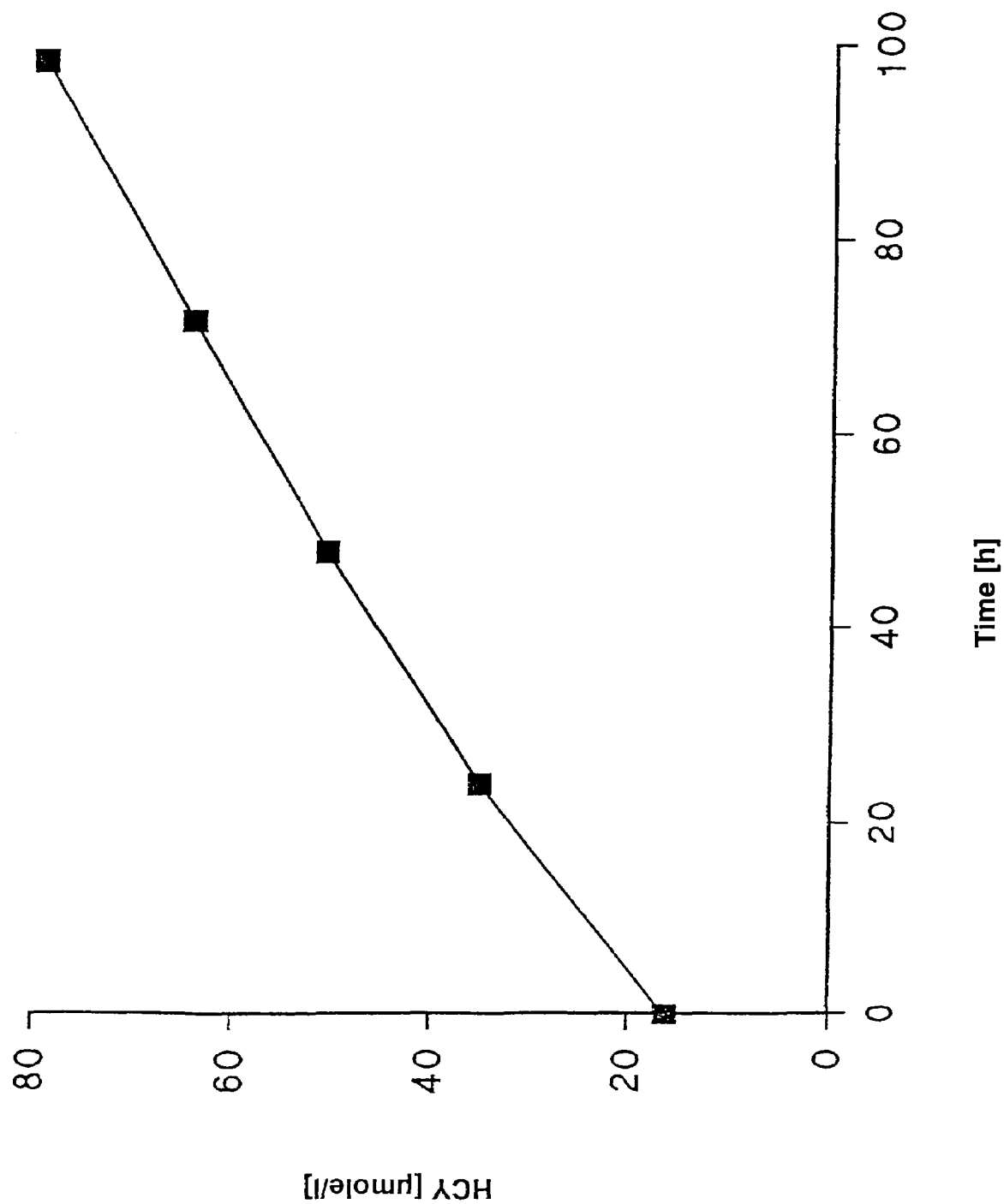
FIG. 2 illustrates the increase of the HCY-concentration in whole blood, which had been collected in vials containing EDTA. The samples where kept at room temperature.

Remarks on Table 1:
\#: amount per ml blood
SD: duration of stabilization;
CS§: lyophilized;
CS: powdered form;
CS*: solution;
A: EDTA + 5(4)-AMCA + DEOA;
Aˢ: A without EDTA;
(−): no stabilization FIGS. 1 and 2 show that by the addition of citric acid and Na-EDTA alone to the samples, no stabilization of the sulphur-containing amino acids (HCY, CYS, CYSGLY, GLU) was obtained. Fumaric acid and ascorbic acid could ensure the stabilization of the HCY-concentration and the CYS-concentration over 40 hours, which is, however, presumably based only on a dilution effect caused by the lysis of erythrocytes.

A mixture of acids and inhibitors, however, proved to be a potent stabilizer for these amino acids (Table 1). The mixture of A and citric acid (Table 1) achieved the best results with respect to the concurrent stabilization of the concentration of HCY, CYS, CYSGLY and GLU over 50 hours (Table 1).

These results are illustrated in FIGS. 2 to 8, compared with data which have been obtained by a stabilization of the

The invention claimed is:

1. A composition for the stabilization of sulphur-containing amino acids and/or for the inhibition of the continuous formation of sulphur-containing amino acids in blood, wherein the sulphur-containing amino acids are selected from the group consisting of homocysteine, cysteine, cysteinyl glycine, glutathione and their derivatives, the composition comprising:

at least one inhibitor, which acts not only in competitive manner, for at least one of the enzymes, S-adenosylhomocysteine hydrolase and methyltransferase, involved in metabolic formation of homocysteine; and in addition to said at least one inhibitor, an anti-coagulant and/or a plasma stabilizer.

2. The composition according to claim 1, the composition being free of agents for the lyses of blood cells.

3. The composition according to claim 1, wherein the inhibitor is non-ionic and/or hydrophobic, so as to be capable of permeating an erythrocyte membrane.

4. The composition according to claim 3, the composition being free of agents for the lyses of blood cells.

5. The composition according to claim 1, wherein the inhibitor is an inhibitor of the S-adenosylhomocysteine hydrolase.

6. The composition according to claim 5, wherein the inhibitor inhibits S-adenosylhomocysteine hydrolase and depletes co-factor NAD.

7. The composition according to claim 1, wherein the inhibitor is selected from a group consisting of neplanocin A, 3-deazaneplanocin A, 9-(trans-2', trans-3'-dihydroxycyclopent-4'-enyl)-adenosine (DHCeA), 3-deaza-DHCeA, 9-(trans-2',trans-3'-dihydroxycyclopentanyl)-adenosine (DHCaA), 3-deaza-DHCaA, β-4'-methyl-DHCaA, β-4'-vinyl-DHCaA, (Z- or E-)4',5'-didehydro-5'-deoxy-5'-fluoro-adenosine (Z-DDFA or E-DDFA), 5'-deoxy-5'-difluoro-adenosine (DFA), and inhibitory derivatives or analogues thereof.

8. The composition according to claim 1, wherein the inhibitor is an irreversible inhibitor.

9. The composition according to claim 1, wherein the inhibitor is a suicide inhibitor.

10. A blood collecting device comprising a collector containing a composition according to claim 1.

11. The blood collecting device according to claim 10, the device being structured and arranged to be connected with a conventional blood withdrawal means.

12. The blood collecting device according to claim 10, the device comprising a monovette.

13. A composition for the stabilization of sulphur-containing amino acids and/or for the inhibition of the continuous formation of sulphur-containing amino acids in blood, wherein the sulphur-containing amino acids are selected from the group consisting of homocysteine, cysteine, cysteine glycine, glutathione and their derivatives, the composition comprising:
an acid;
at least one inhibitor for an enzyme, selected from S-adenosylhomocysteine hydrolase and methyltransferase, which is involved in the metabolic formation of homocysteine; and
in addition to said acid and said at least one inhibitor, an anti-coagulant and/or a plasma stabilizer.

14. The composition according to claim 13, the composition being free of agents for the lyses of blood cells.

15. The composition according to claim 13, wherein the inhibitor is non-ionic and/or hydrophobic, so as to be capable of permeating an erythrocyte membrane.

16. The composition according to claim 15, the composition being free of agents for the lyses of blood cells.

17. The composition according to claim 13, wherein the acid is selected from the group consisting of ascorbic acid, citric acid, citramalic acid, citraconic acid, fumaric acid, lactic acid, oxalic acid and tartaric acid.

18. The composition according to claim 13, wherein the acid is present in powdered form or in lyophilized form.

19. The composition according to claim 13, wherein said inhibitor is an inhibitor of methyl transferase.

20. The composition according to claim 13, wherein said inhibitor is an inhibitor of S-adenosylhomocysteine hydrolase.

21. The composition according to claim 13, wherein the inhibitor is selected from the group consisting of 2'-deoxyadenosine (DEOA), 5(4)-aminoimidazol-4(5)-carboxamide (5(4)-AMCA), 9(S)-(2,3-dihydroxypropyl)-adenosine ((S)-DHPA), (R,S)3-adenin-9-yl-2-hydroxypropane acid ((R,S)-AHPA), adenine-dialdehyde, 5-deazaadenosine, 5-deoxy-5-methyl-thioadenosine, 5-deoxyadenosine (aristeromycin), neplanocin A, 3-deazaneplanocin A, 9-trans-2'-, trans-3'-dihydroxycyclopent-4'-enyl)-adenosine (DHCeA), 3-deaza-DHCeA, 9-(trans-2'-, trans-3'-dihydroxycyclopentanyl)-adenosine (DHCaA), 3-deza-DHCaA, β-4'-methyl-DHCaA, β-4'-vinyl-DHCaA, (Z or E-)4', 5'-didehydro-5'-deoxy-5-fluoro-adenosine (Z-DDFA or E-DDFA), 5'-deoxy-5'-difluoro-adenosine (DFA), and inhibitory derivatives or analogues thereof.

22. The composition according to claim 13, the composition comprising a combination of different inhibitors.

23. The composition according to claim 22, the composition comprising 2'-deoxyadenosine and 5(4)-aminoimidazol-4(5)-carboxamide.

24. The composition according to claim 13, the composition comprising 2-deoxyadenosine and 5(4)-aminoimidazol-4(5)-carboxamide.

25. The composition according to claim 13, the composition further comprising a buffer.

26. A blood collecting device comprising a collector containing a composition according to claim 13.

27. The blood collecting device according to claim 26, the device being structured and arranged to be connected with a conventional blood withdrawal means.

28. The blood collecting device according to claim 27, the device comprising a monovette.

29. A method for the stabilization of sulphur-containing amino acids and/or for the inhibition of the continuous formation of sulphur-containing amino acids in blood, wherein the sulphur-containing amino acids are selected from the group consisting of homocysteine, cysteine, cysteine glycine, glutathione and their derivatives, the method comprising combining a blood sample with an inhibitor of an enzyme involved in the metabolic formation of homocysteine, wherein the inhibitor inhibits an enzyme selected from S-adenosylhomocysteine hydrolase and methyltransferase, and acts not only in a competitive manner for the enzyme.

30. The method according to claim 29, wherein the inhibitor is non-ionic and/or is hydrophobic, so as to be capable of permeating an erythrocyte membrane.

31. The method according to claim 29, wherein the inhibitor is free of agents for the lyses of blood cells.

32. The method according to claim 29, wherein the inhibitor inhibits S-adenosylhomocysteine hydrolase.

33. The method according to claim 32, wherein the inhibitor inhibits S-adenosylhomocysteine hydrolase and depletes co-factor NAD.

34. The method according to claim 29, wherein the inhibitor is selected from the group consisting of neplanocin A, 3-deazaneplanocin A, 9-(trans-2'-, trans-3'-dihydroxycyclopent-4'-enyl)-adenosine (DHCeA), 3-deaza-DHCeA, 9-(trans-2'-, trans-3'-dihydroxycyclopentanyl)-adenosine (DHCaA), 3-deaza-DHCaA, β-4'-methyl-DHCaA, β-4'-vinyl-DHCaA, Z- or E-4', 5'-didehydro-5'-deoxy-5'-fluoro-adenosine (Z-DDFA or E-DDFA), 5'-deoxy-5'-difluoro-adenosine (DFA), and inhibitory derivatives or analogues thereof.

35. A method for the stabilization of sulphur-containing amino acids and/or for the inhibition of the continuous formation of sulphur-containing amino acids in blood, wherein the sulphur-containing amino acids are selected from the group consisting of homocysteine, cysteine, cysteinyl glycine, glutathione and their derivatives, the method comprising inhibiting an enzyme present in a blood sample and involved in the metabolic formation of homocysteine by combining the blood sample with a composition comprising (i) at least one inhibitor, which acts not only in competitive manner, for at least one of the enzymes, selected from S-adenosylhomocysteine hydrolase and methyltransferase, involved in metabolic formation of homocysteine, and in addition to said at least one inhibitor (ii) an anti-coagulant and/or a plasma stabilizer.

36. The method according to claim 35, comprising providing the inhibitor in a concentration range of from about 15 to about 210 μg per 1 ml of the blood sample.

37. The method according to claim 35, further comprising, concurrently with or after the use of the inhibitor, determining the presence of a sulphur-containing amino acid in the blood sample.

38. The method according to claim 37, further comprising, concurrently with or after the use of the inhibitor, determining the presence of a further blood component in the blood sample.

39. A method for the stabilization of sulphur-containing amino acids and/or for the inhibition of the continuous formation of sulphur-containing amino acids in blood, wherein the sulphur-containing amino acids are selected from the group consisting of homocysteine, cysteine, cysteinyl glycine, glutathione and their derivatives, the method comprising inhibiting an enzyme present in a blood sample and involved in the metabolic formation of homocysteine by combining the blood sample with a composition comprising (i) an acid, (ii) at least one inhibitor for an enzyme, selected from S-adenosylhomocysteine hydrolase and methyltransferase, which is involved in the metabolic formation of homocysteine, and in addition to said acid and said at least one inhibitor (iii) an anti-coagulant and/or a plasma stabilizer.

40. The method according to claim 39, comprising providing the inhibitor in a concentration range of from about 15 to about 210 μg per 1 ml of the blood sample.

41. The method according to claim 39, comprising providing the acid in a concentration range or from 2 to 10 mg per 1 ml of the blood sample.

42. The method according to claim 39, further comprising, concurrently with or after the use of the inhibitor, determining the presence of a sulphur-containing amino acid in the blood sample.

43. The method according to claim 42, further comprising, concurrently with or after the use of the inhibitor, determining the presence of a further blood component in the blood sample.

44. A method for the stabilization and/or storage of blood samples having sulphur-containing amino acids, wherein the sulphur-containing amino acids are selected from the group consisting of homocysteine, cysteine, cysteinyl glycine, glutathione and their derivatives, the method comprising obtaining a sample of blood in a container, and inhibiting an enzyme, selected from S-adenosylhomocysteine hydrolase and methyltransferase, involved in the metabolic formation of homocysteine and present in the blood sample by using a composition comprising (i) at least one inhibitor, which acts not only in competitive manner, said enzyme and in addition to said at least one inhibitor (ii) an anti-coagulant and/or a plasma stabilizer.

45. The method according to claim 44, comprising providing the inhibitor in a concentration range of from about 15 to about 210 μg per 1 ml of the blood sample.

46. The method according to claim 44, further comprising, concurrently with or after the use of the inhibitor, determining the presence of a sulphur-containing amino acid in the blood sample.

47. The method according to claim 46, further comprising, concurrently with or after the use of the inhibitor, determining the presence of a further blood component in the blood sample.

48. A method for the stabilization and/or storage of blood samples having sulphur-containing amino acids, wherein the sulphur-containing amino acids are selected from the group consisting of homocysteine, cysteine, cysteinyl glycine, glutathione and their derivatives, the method comprising obtaining a sample of blood in a container, and inhibiting an enzyme selected from S-adenosylhomocysteine hydrolase and methyltransferase, involved in the metabolic formation of homocysteine and present in the blood sample by using a composition comprising (i) an acid, (ii) at least one inhibitor for said enzyme, and in addition to said acid and said at least one inhibitor (iii) an anti-coagulant and/or a plasma stabilizer.

49. The method according to claim 48, comprising providing the inhibitor in a concentration range of from about 15 to about 210 μg per 1 ml of the blood sample.

50. The method according to claim 48, comprising providing the acid is in a concentration range of from 2 to 10 mg per 1 ml of the blood sample.

51. The method according to claim 48, further comprising, concurrently with or after the use of the inhibitor, determining the presence of a sulphur-containing amino acid in the blood sample.

52. The method according to claim 51, further comprising, concurrently with or after the use of the inhibitor, determining the presence of a further blood component in the blood sample.

53. A process for the stabilization of sulphur-containing amino acids and/or for the inhibition of the continuous formation of sulphur-containing amino acids in blood, wherein the sulphur-containing amino acids are selected from the group consisting of homocysteine, cysteine, cysteinyl glycine, glutathione and their derivatives, the process comprising withdrawing blood from a patient, and mixing the withdrawn blood with an inhibitor for an enzyme, selected from S-adenosylhomocysteine hydrolase and methyltransferase, involved in the metabolic formation of homocysteine, wherein the inhibitor acts not only in competitive manner for the enzyme.

54. The process according to claim 53, the process further comprising determining the amount of sulphur-containing amino acids in blood and/or other blood components in the blood sample.

55. The process according to claims 54, the process comprising determining the amount or sulphur-containing amino acid by means of HPLC.

56. The process according to claim 54, the process comprising determining the amount of sulphur-containing amino acid by means of an enzyme immunoassay.

57. The process according to claim 54, the determining step comprising:
(a) placing the inhibitor in a blood collecting device;
(b) placing blood in the blood collecting device;
(c) storing the blood placed in the blood collecting device for a predetermined period wherein the sulphur-containing amino acids are present in a stabilized manner and/or the continuous formation of the sulphur-containing amino acids is inhibited;

(d) determining the amount of sulphur-containing amino acid and optionally further blood components in the blood sample.

58. The process according to claims 57, the process comprising determining the amount of sulphur-containing amino acid by means of HPLC.

59. The process according to claim 57, the process comprising determining the amount of sulphur-containing amino acid by means of an enzyme immunoassay.

60. The process according to claim 57, wherein the steps (a) and (b) are reversed.

61. The process according to claims 60, the process comprising determining the amount of sulphur-containing amino acid by means of HPLC.

62. The process according to claim 60, the process comprising determining the amount of sulphur-containing amino acid by means of an enzyme immunoassay.

63. A process for the stabilization of sulphur-containing amino acids and/or for the inhibition of the continuous formation of sulphur-containing amino acids in blood, wherein the sulphur-containing amino acids are selected from the group consisting of homocysteine, cysteine, cysteinyl glycine, glutathione and their derivatives, the process comprising withdrawing blood from a patient, and mixing the withdrawn blood with a composition comprising (i) at least one inhibitor, which acts not only in competitive manner, for at least one of the enzymes, selected from S-adenosylhomocysteine hydrolase and methyltransferase, involved in metabolic formation of homocysteine, and in addition to said at least one inhibitor (ii) an anti-coagulant and/or a plasma stabilizer.

64. The process according to claim 63, the process further comprising determining the amount of sulphur-containing amino acids and/or other blood components in the blood.

65. The process according to claims 64, the process comprising determining the amount of sulphur-containing amino acid by means of HPLC.

66. The process according to claim 64, the process comprising determining the amount of sulphur-containing amino acid by means of an enzyme immunoassay.

67. The process according to claim 64, the determining step comprising:
(a) placing the inhibitor in a blood collecting device;
(b) placing blood in the blood collecting device;
(c) storing the blood placed in the blood collecting device for a predetermined period wherein the sulphur-containing amino acids are present in a stabilized manner and/or the continuous formation of the sulphur-containing amino acids is inhibited;
(d) determining the amount of sulphur-containing amino acid and optionally further blood components in the blood sample.

68. The process according to claims 67, the process comprising determining the amount of sulphur-containing amino acid by means of HPLC.

69. The process according to claim 67, the process comprising determining the amount of sulphur-containing amino acid by means of an enzyme immunoassay.

70. The process according to claim 67, wherein the steps (a) and (b) are reversed.

71. The process according to claims 70, the process comprising determining the amount of sulphur-containing amino acid by means of HPLC.

72. The process according to claim 70, the process comprising determining the amount of sulphur-containing amino acid by means of an enzyme immunoassay.

73. A process for the stabilization of sulphur-containing amino acids and/or for the inhibition of the continuous formation of sulphur-containing amino acids in blood, wherein the sulphur-containing amino acids are selected from the group consisting of homocysteine, cysteine, cysteinyl glycine, glutathione and their derivatives, the process comprising withdrawing blood from a patient, and mixing the withdrawn blood with a composition comprising (i) an acid, (ii) at least one inhibitor for an enzyme, selected from S-adenosylhomocysteine hydrolase and methyltransferase, which is involved in the metabolic formation of homocysteine, and in addition to said acid and said at least one inhibitor (iii) an anti-coagulant and/or a plasma stabilizer.

74. The process according to claim 73, the process further comprising determining the amount of sulphur-containing amino acids and/or other blood components in the blood.

75. The process according to claims 74, the process comprising determining the amount of sulphur-containing amino acid by means of HPLC.

76. The process according to claim 74, the process comprising determining the amount of sulphur-containing amino acid by means of an enzyme immunoassay.

77. The process according to claim 74, the determining step comprising:
(a) placing the inhibitor in a blood collecting device;
(b) placing blood in the blood collecting device;
(c) storing the blood placed in the blood collecting device for a predetermined period wherein the sulphur-containing amino acids are present in a stabilized manner and/or the continuous formation of the sulphur-containing amino acids is inhibited;
(d) determining the amount of sulphur-containing amino acid and optionally further blood components in the blood sample.

78. The process according to claims 77, the process comprising determining the amount of sulphur-containing amino acid by means of HPLC.

79. The process according to claim 77, the process comprising determining the amount of sulphur-containing amino acid by means of an enzyme immunoassay.

80. The process according to claim 77, wherein the steps (a) and (b) are reversed.

81. The process according to claims 80, the process comprising determining the amount of sulphur-containing amino acid by means or HPLC.

82. The process according to claim 80, the process comprising determining the amount of sulphur-containing amino acid by means of an enzyme immunoassay.

* * * * *